(12) United States Patent
Koehler (10) Patent No.: US 9,011,479 B2
(45) Date of Patent: Apr. 21, 2015

(54) VENA CAVA FILTER WITH BIDIRECTIONAL RETRIEVAL

(76) Inventor: Cleve Koehler, Ellettsville, IN (US)

( * ) Notice: Subject to any disclaimer, the term of this patent is extended or adjusted under 35 U.S.C. 154(b) by 370 days.

(21) Appl. No.: 13/328,663

(22) Filed: Dec. 16, 2011

(65) Prior Publication Data

US 2013/0158591 A1  Jun. 20, 2013

(51) Int. Cl.
*A61M 29/00* (2006.01)
*A61F 2/01* (2006.01)

(52) U.S. Cl.
CPC .............. *A61F 2/01* (2013.01); *A61F 2002/016* (2013.01); *A61F 2220/0083* (2013.01); *A61F 2230/0067* (2013.01); *A61F 2230/0093* (2013.01)

(58) Field of Classification Search
CPC ......... A61B 17/221; A61F 2/07; A61F 2/013; A61F 2/01; A61F 2002/018; A61F 2002/011; A61F 2002/016; A61F 2230/0067; A61F 2230/005; A61F 2230/008; A61F 2230/0078
USPC ......... 606/127, 128, 159, 200, 198, 191, 194, 606/192, 108, 195; 604/96.01, 509, 6.09, 604/107; 623/1.15, 1.16
See application file for complete search history.

(56) References Cited

U.S. PATENT DOCUMENTS

| | | |
|---|---|---|
| 5,324,304 A | 6/1994 | Rasmussen |
| 6,168,603 B1 | 1/2001 | Leslie et al. |
| 6,371,971 B1 | 4/2002 | Tsugita et al. |
| 6,695,865 B2 | 2/2004 | Boyle et al. |
| 6,989,021 B2 | 1/2006 | Bosma et al. |
| 7,101,380 B2 | 9/2006 | Khachin et al. |
| 7,338,512 B2 * | 3/2008 | McGuckin et al. ........... 606/200 |
| 7,736,383 B2 | 6/2010 | Bressler et al. |
| 7,763,044 B2 | 7/2010 | Inoue |
| 7,780,694 B2 | 8/2010 | Palmer et al. |
| 7,785,343 B2 | 8/2010 | Johnson et al. |
| 7,803,171 B1 * | 9/2010 | Uflacker ........................ 606/200 |
| 2003/0100917 A1 * | 5/2003 | Boyle et al. ................... 606/200 |
| 2003/0208224 A1 * | 11/2003 | Broome ........................ 606/200 |
| 2004/0087999 A1 | 5/2004 | Bosma et al. |
| 2005/0055046 A1 | 3/2005 | McGuckin, Jr. et al. |
| 2006/0041271 A1 | 2/2006 | Bosma et al. |
| 2008/0275487 A1 | 11/2008 | Fleming |
| 2009/0005803 A1 | 1/2009 | Batiste |
| 2009/0043332 A1 | 2/2009 | Sullivan et al. |
| 2009/0062840 A1 | 3/2009 | Angel |
| 2009/0299403 A1 * | 12/2009 | Chanduszko et al. ........ 606/200 |
| 2010/0268264 A1 | 10/2010 | Bonnette et al. |
| 2011/0160763 A1 | 6/2011 | Ferrera et al. |
| 2012/0083823 A1 * | 4/2012 | Shrivastava et al. .......... 606/200 |
| 2012/0109180 A1 * | 5/2012 | Shrivastava ................... 606/200 |

* cited by examiner

*Primary Examiner* — Jocelin Tanner
(74) *Attorney, Agent, or Firm* — Brinks Gilson & Lione (57) ABSTRACT

An intravascular filter configured for bidirectional retrieval and a method for retrieving the filter from a patient's vena cava through the patient's femoral vein.

14 Claims, 7 Drawing Sheets

VENA CAVA FILTER WITH BIDIRECTIONAL RETRIEVAL

BACKGROUND

The present invention relates to medical devices. More particularly, the invention relates to a removable intravascular filter that can be removed from the vena cava of a patient through the patient's jugular or femoral vein.

Filtering devices that are percutaneously placed in the vena cava have been available for a number of years. A need for such filtering devices arises in trauma patients, orthopedic surgery patients, neurosurgery patients, or in patients having medical conditions requiring bed rest or non-movement. Patients having such medical conditions face an increased risk of thrombosis in the peripheral vasculature, wherein thrombi break away from the vessel wall, risking downstream embolism or embolization. For example, depending on the size, such thrombi pose a serious risk of pulmonary embolism wherein blood clots migrate from the peripheral vasculature through the heart and into the lungs.

Historically, vena cava filters were considered to be permanent implants and remained implanted in the patient for life. More recently, removable vena cava filters have been developed. These filters may be removed from the patient's vena cava after the condition or medical problem that required the device has passed.

The benefits of vena cava filters, and particularly removable vena cava filters, have been well established, but improvements may be made. For example, the vast majority of the removable vena cava filters currently on the market must be removed through the patient's jugular vein. In some instances, however, removal through the patient's femoral vein is preferable to removal through the jugular vein. For example, filters sometimes shift or become stuck in a patient's vena cava. The ability to retrieve such troublesome filters from a different access point can increase the likelihood that they will be removed successfully. In addition, jugular retrieval requires that a retrieval sheath be advanced through the patient's heart, which is contraindicated in some cases. Finally, scarring at the access point is less noticeable when retrieval is initiated through the femoral vein.

It has been a challenge to design a vena cava filter suitable for removal through a patient's femoral vein.

SUMMARY OF INVENTION

The present invention generally relates to an intravascular filter configured for bidirectional retrieval. The invention also relates to a method of removing an intravascular filter from a patient's vena cava via the patient's femoral vein.

In one embodiment incorporating the principles of the present invention, an intravascular filter configured for bidirectional retrieval is provided. The intravascular filter includes a plurality of primary struts having first and second ends. The first ends are attached together along a longitudinal axis to define a downstream end of the filter, and the primary struts extend upstream from the first ends to the second ends. A lattice portion having upstream and downstream edges is substantially cylindrically disposed about the longitudinal axis. The second ends of the primary struts adjoin the downstream edge of the lattice portion. The intravascular filter also includes a plurality of secondary struts having third and fourth ends. The third ends of the secondary struts adjoin the upstream edge of the lattice portion, and the secondary struts extend upstream to the fourth ends. The fourth ends are attached together along the longitudinal axis to define an upstream end of the filter. A first coupling element is disposed at the downstream end of the filter for jugular vein retrieval, and a second coupling element is disposed at the upstream end of the filter for femoral vein retrieval.

An intravascular filter constructed in accordance with the principles of the present invention may be retrieved from a patient's vena cava via the patient's femoral vein. A retrieval assembly including a retrieval sheath and a control member is percutaneously inserted into the patient's vasculature through the patient's femoral vein. The retrieval assembly is advanced through the patient's vasculature to a retrieval position proximal to the intravascular filter in the patient's vena cava. The control member is attached to the second coupling element to hold the intravascular filter in position, and then the retrieval sheath is advanced distally over the intravascular filter. The retrieval assembly and the intravascular filter are then removed from the patient's vasculature.

Further objects, features, and advantages of the present invention will become apparent from consideration of the following description and the appended claims when taken in connection with the accompanying drawings.

DETAILED DESCRIPTION

The present invention generally relates to an intravascular filter configured for bidirectional retrieval. Thus, when a filter constructed in accordance with the principles of the present invention is implanted in a patient's vena cava, a medical practitioner retrieving the filter has the option of removing the filter through the patient's jugular or femoral vein. The invention also relates to a method of removing an intravascular filter from a patient's vena cava via the patient's femoral vein.

As used herein, the terms "upstream" and "downstream" refer to the direction of blood flow in a patient's vasculature. When these terms are used to describe the elements of an intravascular filter, they suggest a preferred orientation of the filter in the patient's vasculature. However, these terms are not intended to be limiting in this regard. In other words, a filter otherwise including the structural elements recited herein will not be deemed to fall outside the scope of the present invention merely because it is implanted in a different orientation.

Figure 1:
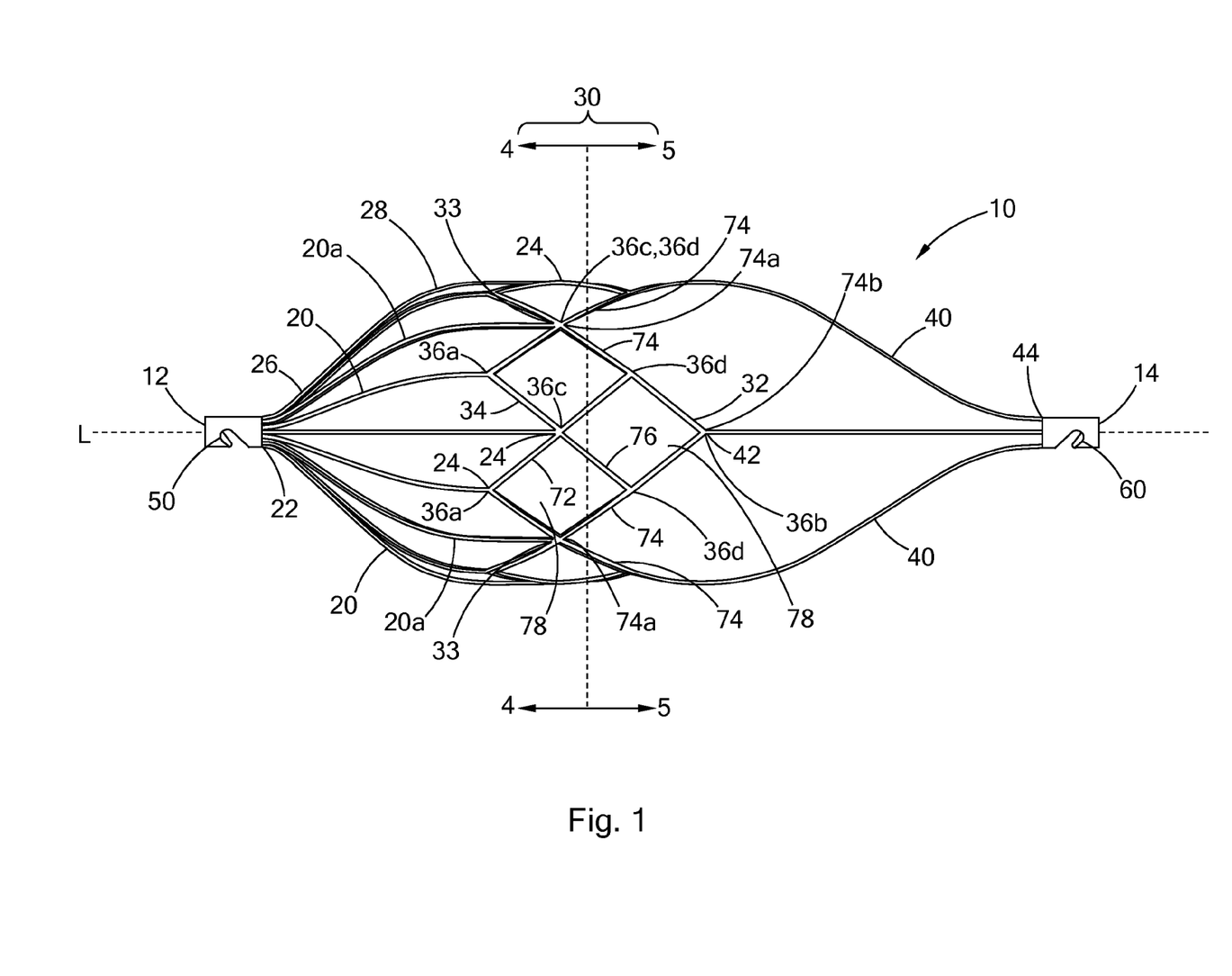
FIG. 1 is a side view of an intravascular filter in an expanded state in accordance with the principles of the present invention.
Figure 2:
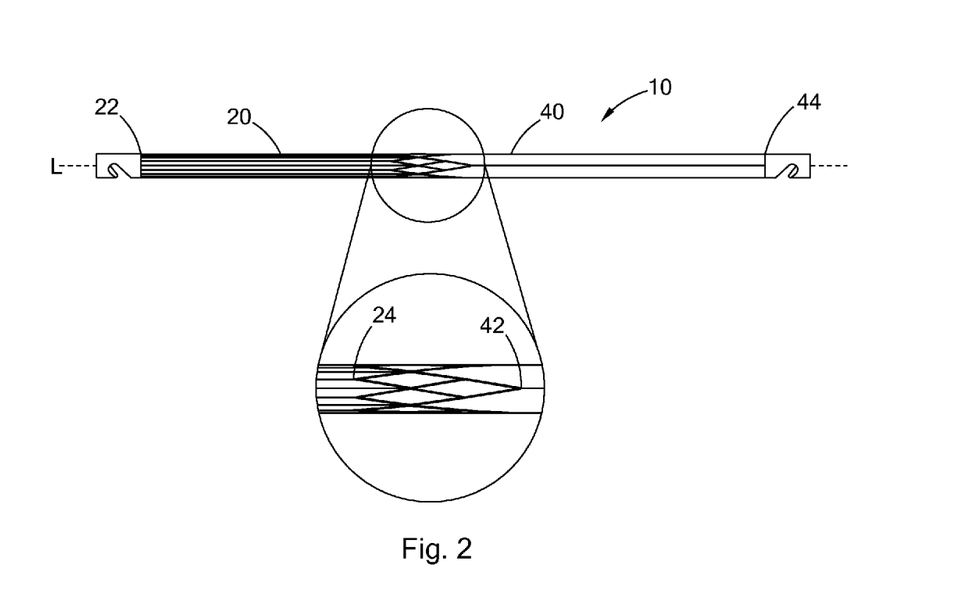
FIG. 2 is a side view of the filter seen in FIG. 1 in a collapsed state.
Figure 3:
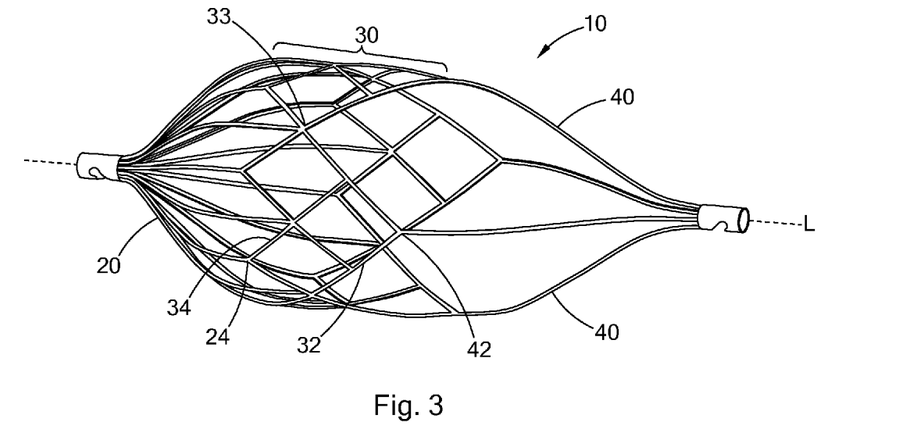
FIG. 3 is a perspective view of the filter seen in FIG. 1.

FIGS. 1 and 2 illustrate side views of an intravascular filter 10 constructed in accordance with the principles of the present invention. FIG. 3 illustrates a perspective view of the filter 10. FIG. 1 illustrates the filter 10 in an expanded state for capturing thrombi in a patient's blood vessel. FIG. 2 illustrates the filter 10 in a collapsed state for delivery to and retrieval from the patient's blood vessel. As discussed in greater detail below, the filter 10 is preferably biased to self-expand to the expanded state upon delivery to the patient's blood vessel.

Referring to FIGS. 1 and 2, the filter 10 has a downstream end 12, an upstream end 14, a plurality of primary struts 20, a lattice portion 30, and a plurality of secondary struts 40. The primary struts 20 extend from the downstream end 12 of the filter 10 to the lattice portion 30. The secondary struts 40 extend from the lattice portion 30 of the filter 10 to the upstream end 14 of the filter 10.

As best seen in FIG. 3, the primary and secondary struts 20 and 40 are substantially evenly spaced about the longitudinal axis L, and the lattice portion 30 is substantially cylindrically disposed about the longitudinal axis L. For the sake of clarity, however, only those portions of the filter 10 closest to the viewer are shown in FIGS. 1 and 2.

The primary struts 20 define a downstream filtering portion of the filter 10. Each primary strut 20 has a first end 22 and a second end 24. The first ends 22 are attached together along the longitudinal axis L of the filter 10 to define the downstream end 12 of the filter 10. Each primary strut 20 extends upstream from its first end 22 to its second end 24. The primary struts 20 may all have the same length, or the primary struts 20 may vary in length without falling beyond the scope of the invention.

As shown in FIG. 1, each primary strut 20 preferably extends arcuately in a longitudinal plane from its first end 22 to its second end 24 when the filter 10 is in the expanded state. Each primary strut 20 includes a first arc 26 and a second arc 28. The first arc 26 extends from the first end 22 of the primary strut 20 away from the longitudinal axis L. The second arc 28 extends from the first arc 26 toward the longitudinal axis L and terminates at the second end 24 of the primary strut 20.

When the filter 10 is in the collapsed state, as shown in FIG. 2, each primary strut 20 preferably extends from its first end 22 to its second end 24 substantially in parallel with the longitudinal axis L. As used herein, a primary strut 20 shall be deemed to extend "substantially in parallel" to the longitudinal axis L if the angle between the longitudinal axis and a line passing through the first and second ends 22 and 24 of the primary strut 20 does not exceed 10°.

The lattice portion 30 of the filter 10 connects the primary struts 20 to the secondary struts 40, imparts rigidity to the filter 10, and provides a radial force against the walls of a patient's blood vessel to hold the filter 10 in place in the blood vessel. As used herein, the term "lattice portion" refers to a lattice of interconnected connecting members. A lattice portion that is substantially cylindrically disposed about an axis has two edges disposed at the two ends of the substantially cylindrical structure. The two edges of such a lattice portion may intersect at one or more points, or coincide in one or more regions, about the circumference of the lattice portion, but they do not coincide about the entire circumference of the lattice portion.

As most clearly seen in FIG. 3, the lattice portion 30 of the filter 10 is substantially cylindrically disposed about the longitudinal axis L of the filter 10. The lattice portion 30 has upstream and downstream edges 32 and 34. The second ends 24 of the primary struts 20 adjoin the downstream edge 34 of the lattice portion 30. The third ends 42 of the secondary struts 40 adjoin the upstream edge 32 of the lattice portion 30. The upstream and downstream edges 32 and 34 of the lattice portion 30 coincide at several points of coincidence 33, but the upstream edge 32 is generally disposed upstream of the downstream edge 34.

As shown in FIG. 1, the lattice portion 30 of the filter 10 comprises a plurality of interconnected connecting members, including a plurality of first, second, and third connecting members 72, 74, and 76, respectively. Each connecting member is defined below by reference to the structures connected by the given connecting member, not by the method of constructing the connecting member. Thus, it will be understood that a single connecting member may be constructed from either a single, unitarily formed element or from more than one element fixedly attached together in series.

The connecting members 72, 74, and 76 adjoin one another and the primary and secondary struts 20 and 40 at a plurality of vertices 36. The plurality of vertices 36 shown in FIG. 1 includes prominent downstream vertices 36a, prominent upstream vertices 36b, non-prominent downstream vertices 36c, and non-prominent upstream vertices 36d. As used herein, a "prominent downstream vertex" is defined as a vertex from which at least one connecting member extends upstream, and no connecting members extend downstream. A "prominent upstream vertex" is defined as a vertex from which at least one connecting member extends downstream, and no connecting members extend upstream. A "non-prominent downstream vertex" refers to a vertex disposed on the downstream edge 34 of the lattice portion 30 from which at least one connecting member extends upstream, and at least one connecting member extends downstream. A "non-prominent upstream vertex" refers to a vertex disposed on the upstream edge 32 of the lattice portion 30 from which at least one connecting member extends upstream, and at least one connecting member extends downstream. In the filter 10 shown in FIG. 1, each point of coincidence 33 is both a non-prominent downstream vertex 36c and a non-prominent upstream vertex 36d.

In the filter 10, a primary strut 20 adjoins each prominent downstream vertex 36a, and a secondary strut 40 adjoins each prominent upstream vertex 36b, so that a sheath may slide over the filter 10 in either direction without catching on a prominent vertex 36a or 36b during the retrieval of the filter 10. Additional primary struts 20 also adjoin the non-prominent downstream vertices 36c of the lattice portion 30. In contrast, additional secondary struts 40 do not adjoin the non-prominent upstream vertices 36d of the lattice portion 30.

As will be apparent to a person having ordinary skill in the relevant art, the lattice portion 30 of the filter 10 has been configured to provide an appropriate ratio of prominent and non-prominent downstream vertices 36a and 36c to prominent upstream vertices 36b based on the desired numbers of primary and secondary struts 20 and 40. Modifications to the configuration of the lattice portion 30 may be made to accommodate different ratios of primary and secondary struts 20 and 40 without falling beyond the scope of the present invention.

As shown in FIG. 1, the connecting members 72, 74, and 76 making up the lattice portion 30 of the filter 10 define a plurality of cells 78 bounded on each side by a connecting member. This structure imparts stability and rigidity to the filter 10. The connecting members defining the cells 78 also provide a radial force against the walls of a patient's blood vessel to hold the filter 10 in place in the blood vessel. The cells 78 may each have a diamond shape, as shown in FIG. 1, when the filter 10 is in the expanded state. However, the cells may alternatively have any other suitable shape, as dictated by the arrangement of the connecting members, without falling outside the scope of the present invention.

Each first connecting member 72 extends between the second ends 24 of adjacent primary struts 20. As shown in FIG. 1, the first connecting members 72 of the filter 10 connect the second end 24 of each primary strut 20 to the second ends 24 of both adjacent primary struts 20, such that the first connecting members 72 define the downstream edge 34 of the lattice portion 30 of the filter 10. However, it will be understood that the first connecting members 72 may connect less than all of the second ends 24 of the primary struts 20 without falling beyond the scope of the present invention.

Each second connecting member 74 of the filter 10 adjoins the second end 24 of one of the primary struts 20 and extends to the third end 42 of one of the secondary struts 40. The second connecting members 74 each have a primary end 74a adjoining the second end 24 of the primary strut 20 and a secondary end 74b adjoining the third end 42 of the secondary strut. Two second connecting members 74 adjoin the third end 42 of each secondary strut 40 at a prominent upstream vertex 36b.

Preferably, as shown in FIG. 1, exactly two second connecting members 74 adjoin the second end 24 of every fourth primary strut 20a, and no second connecting members 74 adjoin any other primary strut 20. Thus, because two second connecting members 74 adjoin each secondary strut 40, and because there are only two second connecting members 74 for every four primary struts 20, this configuration of second connecting members 74 is compatible with a filter 10 that has four times as many primary struts 20 as secondary struts 40.

Each third connecting member 76 extends upstream from the second end 24 of one of the primary struts 20 and adjoins one of the second connecting members 74. As shown in FIG. 1, the third connecting member 76 adjoins the second connecting member 74 between the primary and secondary ends 74a and 74b of the second connecting member 74 at a non-prominent upstream vertex 36d.

As shown in FIG. 1, the connecting members 72, 74, and 76 making up the lattice portion 30 of the filter 10 are configured to define groupings of three adjoining cells 78. The groupings of cells 78 are separated by points of coincidence 33. However, it will be understood that other configurations of the connecting members are possible, consistent with the definitions of the first, second, and third connecting members set forth above, without falling beyond the scope of the present invention.

Figure 1A:
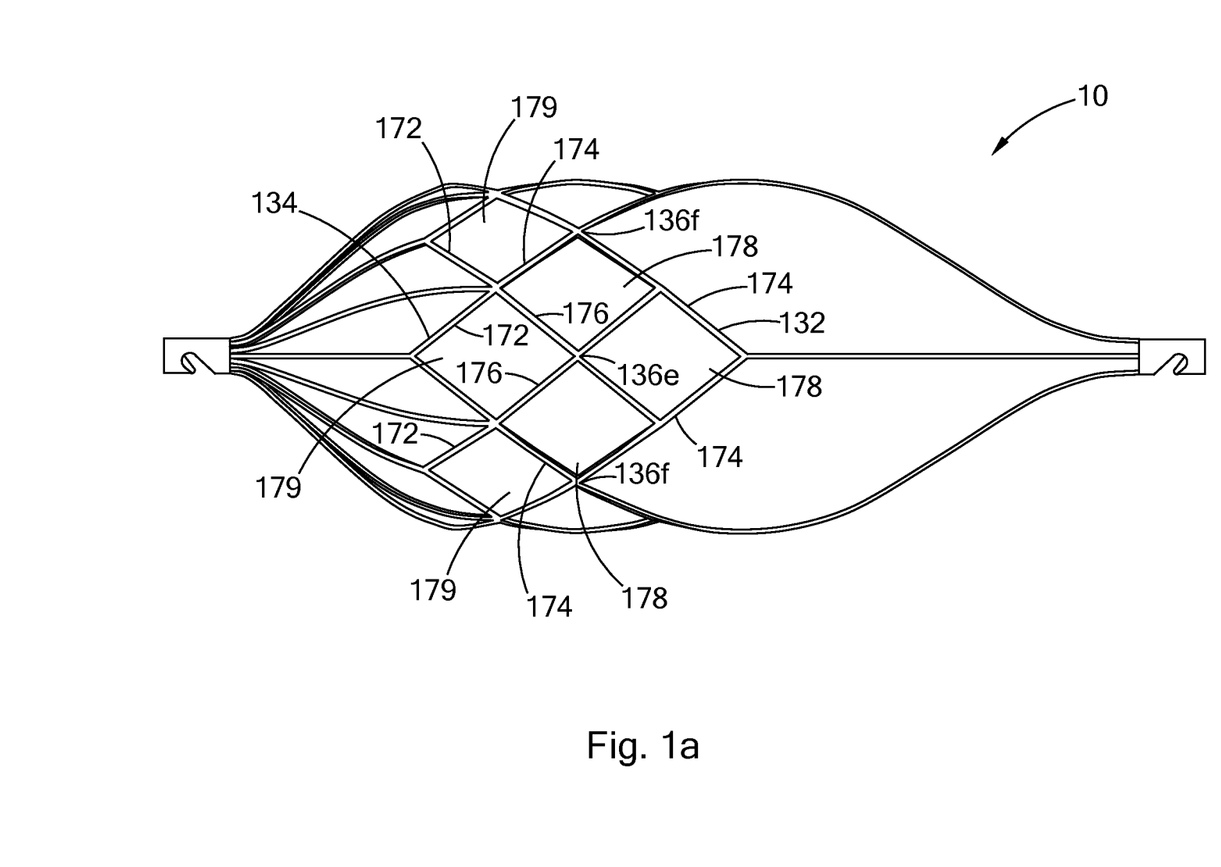

For example, as shown in FIG. 1a, the connecting members 172, 174, and 176 making up the lattice portion 130 of the filter 110 are configured to define an additional row of cells 179 disposed downstream of the groupings of three adjoining cells 178. This configuration of cells 178 and 179 is advantageous where additional rigidity and/or additional radial force against the walls of the patient's blood vessel are desired. In the filter 110, the upstream and downstream edges 132 and 134 of the lattice portion 130 do not coincide in any regions about the circumference of the filter 110. In this configuration, the third connecting members 176 intersect one another at interior vertices 136e. The second connecting members 174 intersect one another at vertices 136f. Other configurations of the first, second, and third connecting members, defining other configurations of cells, are also possible without falling beyond the scope of the present invention.

The secondary struts 40 define an upstream support portion of the filter 10. Each secondary strut 40 has a third end 42 and a fourth end 44. The third ends 42 of the secondary struts 40 adjoin the upstream edge 32 of the lattice portion 30. Each secondary strut 40 extends upstream from its third end 42 to its fourth end 44. The fourth ends 44 of the secondary struts 40 are attached together along the longitudinal axis L of the filter 10 to define the upstream end 14 of the filter 10. The secondary struts 40 may all have the same length, or the secondary struts 40 may vary in length without falling beyond the scope of the invention. Preferably, the secondary struts 40 are longer than the primary struts 20.

As shown in FIG. 1, each secondary strut 40 preferably extends arcuately in a longitudinal plane toward the longitudinal axis L from its third end 42 to its fourth end 44 when the filter 10 is in the expanded state. When the filter 10 is in the collapsed state, as shown in FIG. 2, the secondary struts 40 preferably extend substantially in parallel with the longitudinal axis L from their third ends 42 to their fourth ends 44. As used herein, a secondary strut 40 shall be deemed to extend "substantially in parallel" to the longitudinal axis L if the angle between the longitudinal axis and a line passing through the third and fourth ends 42 and 44 of the secondary strut 40 does not exceed 10°.

Figure 4:
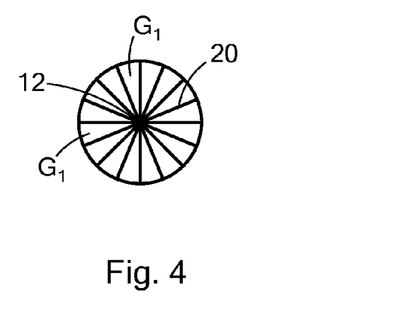
FIG. 4 is a cross-sectional view of the filter seen in FIG. 1, taken along the line 4-4.

FIG. 4 illustrates a downstream-facing cross-sectional view of the filter 10 taken along the line 4-4 in FIG. 1. Viewed from this vantage point, the primary struts 20 extend radially from the downstream end 12 of the filter 10. The primary struts 20 define a plurality of first gaps $G_1$. The number of primary struts 20, and the configuration of the primary struts 20, are chosen to provide first gaps $G_1$ that are sufficiently large to allow the patient's blood to flow unimpeded through the filter 10, but sufficiently small to capture thrombi in the patient's blood vessel.

Figure 5:
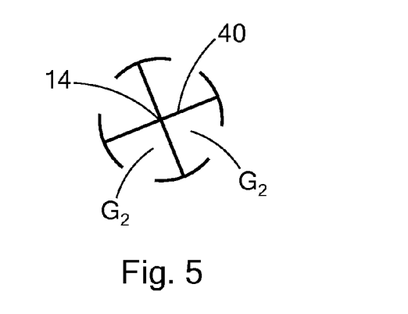
FIG. 5 is a cross-sectional view of the filter seen in FIG. 1, taken along the line 5-5.

FIG. 5 illustrates an upstream-facing cross-sectional view of the filter 10 taken along the line 5-5 in FIG. 1. Viewed from this vantage point, the secondary struts 40 extend radially from the upstream end 14 of the filter 10. The secondary struts 40 define a plurality of second gaps $G_2$. The number of secondary struts 40, and the configuration of the secondary struts 40, are chosen to provide second gaps $G_2$ that are sufficiently large to allow thrombi in the patient's blood vessel to pass into the interior of the filter. Preferably, the number of secondary struts 40 is smaller than the number of primary struts 20. More preferably, the filter 10 has four times as many primary struts 20 as secondary struts 40. For example, as shown in FIGS. 4 and 5, the filter 10 may have sixteen primary struts 20 and four secondary struts 40.

Figure 6:
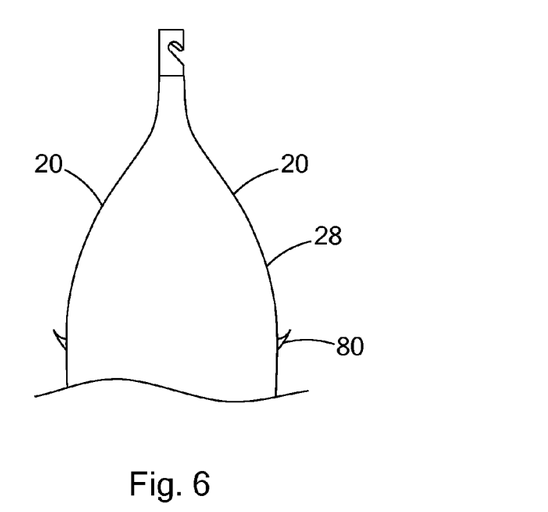
FIG. 6 is a partial side view of the filter seen in FIG. 1, showing some of the primary struts of the filter in the expanded state.
Figure 7:
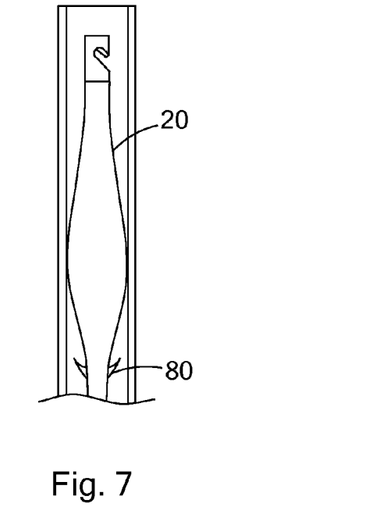
FIG. 7 is a partial side view of the filter seen in FIG. 1, showing some of the primary struts of the filter in the collapsed state.

Referring now to FIGS. 6 and 7, the filter 10 may further comprise one or more anchoring hooks 80 disposed on one or more of the primary struts 20 to hold the filter in position in a patient's blood vessel. FIGS. 6 and 7 depict partial side views of the filter 10 in the expanded and collapsed states, respectively, in which only a few of the primary struts 20 are shown. The lattice portion 30 and secondary struts 40 are not shown in FIGS. 6 and 7. As shown in FIG. 6, the anchoring hooks 80 may be disposed on the second arc 28 of the primary struts 20, and each anchoring hook 80 may extend outwardly and upstream from its point of attachment with the primary strut 20.

Preferably, the primary struts 20 are shaped such that the anchoring hooks 80 do not interfere with the delivery or retrieval of the filter 10. For example, as shown in FIG. 7, the arcuate shape of the primary struts 20 may result in the second arc 28 of the filter 10 bending inwardly when the filter 10 is in the collapsed state. This inward bend prevents the anchoring hooks 80 from contacting the inner wall of a delivery or retrieval sheath. The concern that the anchoring hooks 80 in the collapsed state may scrape, scratch, or tear the inner wall of the delivery or retrieval sheath is eliminated, simplifying delivery and retrieval of the filter 10.

The filter 10, including the primary struts 20, lattice portion 30, and secondary struts 40, may be constructed from any suitable material and by any means known to those having ordinary skill in the relevant art without falling beyond the scope of the present invention. Preferably, the filter 10 is constructed from a superelastic material, nitinol, stainless steel, cobalt-chromium-nickel-molybdenum-iron alloy, cobalt-chrome alloy, or nickel-chromium alloy.

In some embodiments, the filter 10 is constructed from a laser cut nitinol cannula. The nitinol cannula from which the filter 10 is cut may have a diameter between about 1.5 mm and about 2.5 mm, and preferably has a diameter between about 1.7 mm and about 2.0 mm. In these embodiments, the filter 10 may, but need not, further comprise downstream and upstream hubs housing the ends of the nitinol cannula at the downstream and upstream ends 12 and 14 of the filter 10.

In other embodiments, the filter 10 is constructed from woven or welded stainless steel, nitinol, or nickel-chromium (e.g., INCONEL®) wire. In these embodiments, the filter 10 preferably further comprises a downstream hub disposed at the downstream end 12 of the filter 10 and housing the first ends 22 of the primary struts 20, as well as an upstream hub disposed at the upstream end 14 of the filter 10 and housing the fourth ends 44 of the secondary struts 40.

In one embodiment, the primary struts 20, lattice portion 30, and secondary struts 40 of the filter 10 may be constructed from a nitinol or nickel-chromium alloy having a martensitic-austenitic transition temperature that is slightly below human body temperature. The filter 10 may be in the collapsed state when the alloy material is in its martensitic state. Conversely, the filter may be in the expanded state when the alloy material is in its austenitic state. In this embodiment, the filter 10 may be maintained at a low temperature prior to insertion into the body, such that the filter 10 remains in the collapsed state. Upon delivery to a desired body location, the filter may be allowed to warm to a temperature exceeding the transition temperature so that the filter undergoes a martensitic-austenitic transition and assumes the expanded state.

Figure 8A:
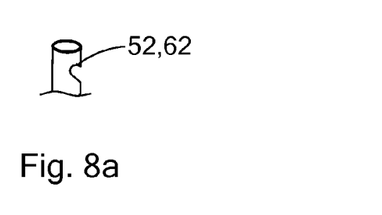
FIGS. 8a and 8b are partial side views of two embodiments of the filter seen in FIG. 1, showing two different coupling element designs.
Figure 8B:
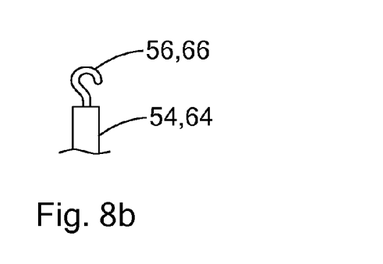

Referring again to FIGS. 1, 2, and 8*a-b*, the filter 10 also has a first coupling element 50 disposed at the downstream end 12 for jugular vein retrieval and a second coupling element 60 disposed at the upstream end 14 for femoral vein retrieval. For example, as shown in FIG. 8*a*, where the filter 10 is constructed from a laser cut nitinol cannula, the coupling elements 50 and 60 may comprise diagonal notches 52 and 62, respectively, in the walls of the nitinol cannula. Alternatively, as shown in FIG. 8*b*, the coupling elements 50 and 60 may comprise a jugular retrieval hook 56 extending downstream from the downstream hub 54 and a femoral retrieval hook 66 extending upstream from the upstream hub 64, respectively.

The dimensions of an intravascular filter constructed in accordance with the principles of the present invention may be selected by a person having ordinary skill in the relevant art as appropriate for a particular application. Such selection does not require undue experimentation. For example, referring again to FIG. 1, the length of the filter 10, defined as the distance between the downstream end 12 and the upstream end 14, measured along the longitudinal axis L when the filter 10 is in the expanded state may be between about 65 mm and about 85 mm, preferably between about 70 mm and about 80 mm. The width of the filter 10, measured perpendicular to the longitudinal axis across the lattice portion 30 when the filter 10 is in the expanded state may be between about 13 mm and about 30 mm, preferably between about 18 mm and about 25 mm. The distance across the diamond-shaped cells 78 in the lattice portion 30 of the filter 10 may be between about 8 mm and about 15 mm, preferably between about 10 mm and about 13 mm, when the filter 10 is in the expanded state. The primary and secondary struts 20 and 40, and the connecting members 72, 74, and 76 may have a diameter between about 0.2 mm and about 0.5 mm, preferably between about 0.3 mm and about 0.4 mm. The foregoing dimensions are merely exemplary. An intravascular filter constructed in accordance with the principles of the present invention may have any other suitable dimensions without falling beyond the scope of the present invention.

An intravascular filter constructed in accordance with the principles of the present invention, such as the filter 10, may be delivered to a patient's blood vessel, such as the patient's vena cava, using standard techniques familiar to those having ordinary skill in the relevant art. For example, a delivery sheath may be percutaneously inserted into the patient's vasculature via any suitable access site, such as the jugular vein, femoral vein, or any other suitable access site. The delivery sheath then may be advanced through the patient's vasculature until the distal end of the delivery sheath is disposed in the patient's blood vessel at the desired site of deployment. The intravascular filter then may be disposed within the lumen of the delivery sheath and expelled from the distal end of the delivery sheath by use of a push wire or other suitable device. Upon deployment from the distal end of the delivery sheath, the filter preferably self-expands to the expanded state as discussed above. While the foregoing method is provided by way of example, a person having ordinary skill in the relevant art will understand that a filter constructed in accordance with the principles of the present invention may be deployed using any other suitable technique without falling outside the scope of the present invention.

Figure 9:
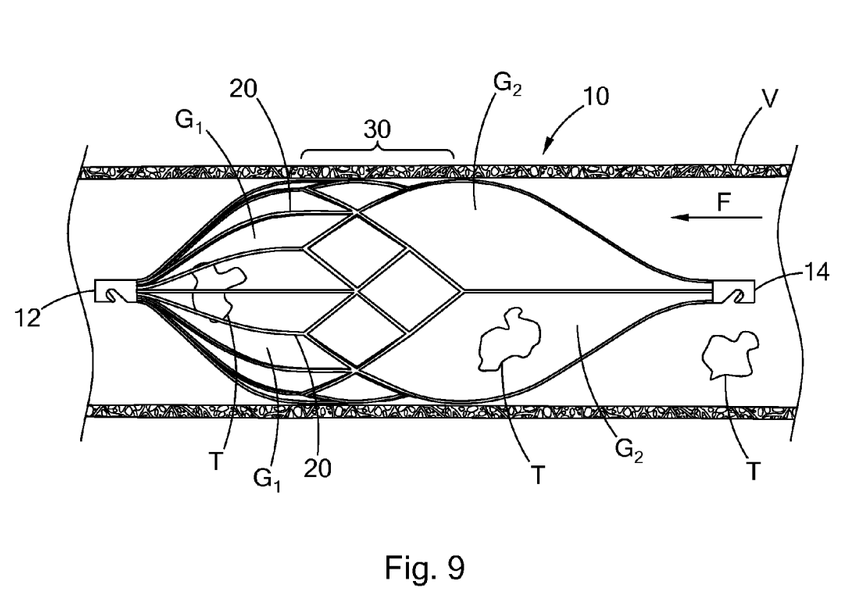
FIG. 9 is an environmental view of the filter seen in FIG. 1 filtering thrombi in a patient's blood vessel.

FIG. 9 illustrates the filter 10 deployed in the expanded state in a patient's blood vessel V. The direction of blood flow in the blood vessel is indicated by the arrow F. As shown in FIG. 9, the filter 10 is preferably deployed with the downstream end 12 of the filter 10 disposed downstream of the upstream end 14 of the filter 10. Thrombi T carried in the patient's blood stream pass through the second gaps $G_2$ defined by the secondary struts 40 and enter the interior of the filter. As the thrombi T are carried further downstream, they pass through the lattice portion 30 of the filter 10 enter the filtering portion of the filter 10 defined by the primary struts 20. The thrombi T are too large to pass through the first gaps $G_1$ between the primary struts 20 and therefore remain captured in the filtering portion of the filter 10. As the flow of blood pushes the thrombi T against the primary struts 20, the thrombi T slide downstream along the primary struts 20, approaching the downstream end 12 of the filter 10. Due to the curvature of the primary struts 20, the thrombi T are simultaneously guided toward the longitudinal axis of the filter 10 and come to rest near the center of the blood vessel V.

The ability of the filter 10 to capture thrombi in the center of the patient's blood vessel provides several advantages. First, a clot in the center of the blood vessel creates less blood flow disruption and vessel trauma than a blood clot trapped against the vessel wall. Second, blood flow is greatest at the center of the blood vessel, and therefore a clot is more likely to break down if it is trapped in the center of the vessel than if it is trapped along a blood vessel wall. Third, clots trapped along a blood vessel wall may grow larger, which can increase the risk of total occlusion in the blood vessel.

After the need for intravascular filtration has passed, an intravascular filter constructed in accordance with the principles of the present invention may be removed from the patient's blood vessel. Where the intravascular filter has been deployed in the patient's vena cava, the filter may be removed via the patient's jugular vein using standard techniques familiar to those having ordinary skill in the relevant art.

Figure 10:
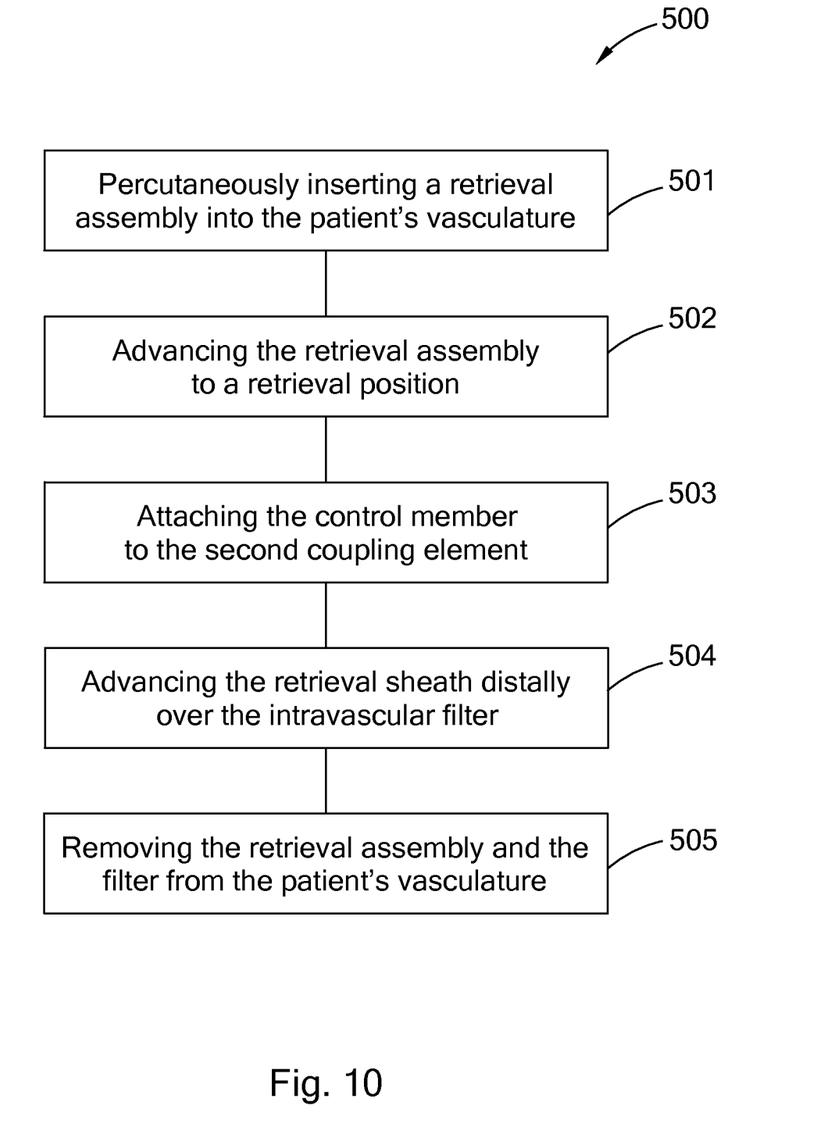
FIG. 10 is a flow chart depicting a method of retrieving the intravascular filter of the present invention from a patient's vena cava via the patient's femoral vein.

FIG. 10 is a flow chart depicting a method 500 for retrieving an intravascular filter from a patient's vena cava through the patient's femoral vein in accordance with the principles of the present invention. As indicated in box 501, the method 500 comprises percutaneously inserting a retrieval assembly into the patient's vasculature through the patient's femoral vein. The retrieval assembly preferably includes a retrieval sheath and a control member. The retrieval sheath has a proximal sheath end, a distal sheath end, and a sheath lumen formed therethrough. The control member may have any structure suitable to attach to the second coupling element of the filter. Preferably, the control member is an elongate member having a proximal member end, a distal member end, and a snare loop attached to the distal member end. In use, the control member is preferably disposed in the sheath lumen of the retrieval sheath.

The components of the retrieval assembly may be inserted into the patient's vasculature in any order, or simultaneously, without falling beyond the scope or spirit of the present invention. For example, the control member may be disposed in the sheath lumen of the retrieval sheath, and the entire retrieval assembly may be inserted into the patient's vasculature simultaneously. Alternatively, the retrieval sheath may be inserted into the patient's vasculature, and then the control member may be inserted into the sheath lumen of the retrieval sheath. The components of the retrieval assembly may be inserted into the patient's vasculature in any other order without falling beyond the scope of the present invention.

As indicated in box 502, the method 500 further comprises advancing the retrieval assembly through the patient's vasculature to a retrieval position proximal to the filter. As described above in connection with the step of inserting the retrieval assembly into the patient's vasculature, the components of the retrieval assembly may be advanced through the patient's vasculature in any order, or simultaneously, without falling beyond the scope of the present invention.

Figure 11A:
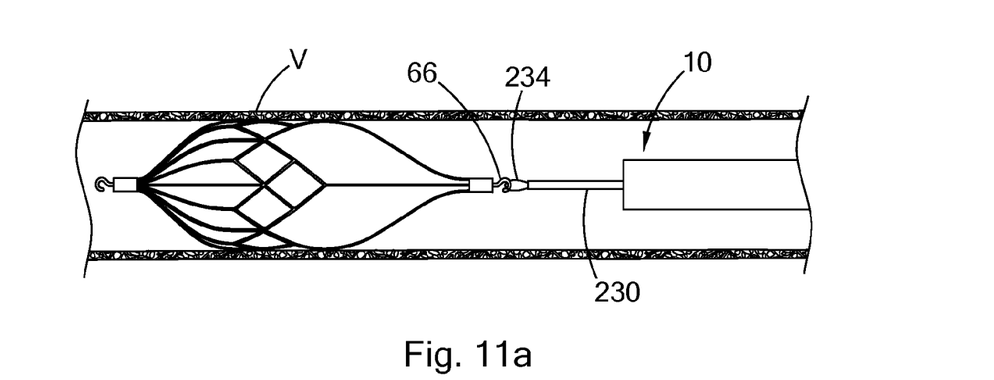
FIGS. 11a-11c are environmental views showing an intravascular filter being retrieved from a patient's vena cava in accordance with the principles of the present invention.

As indicated in box 503, and as illustrated in FIG. 11a, the method 500 further comprises attaching the control member 230 to the second coupling element 60 of the filter 10. As discussed above with reference to FIGS. 8a-b, the second coupling element of the filter 10 may be a diagonal notch or a femoral retrieval hook 66. Thus, if the control member includes a snare loop 234, the step of attaching the control member 230 to the second coupling element may involve placing the snare loop 234 into the diagonal notch or over the femoral retrieval hook 66. After the control member 230 has been attached to the second coupling element, the filter 10 may be held in a steady and stationary position by holding the control member 230 in a stationary position.

Figure 11B:
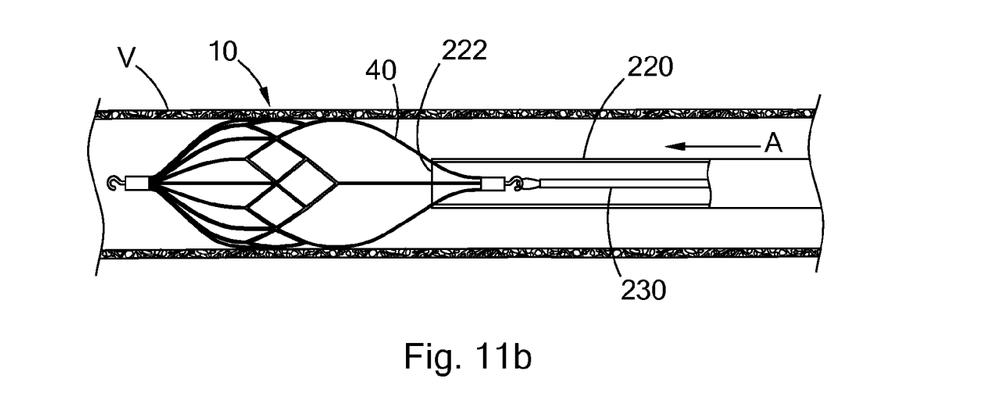
Figure 11C:
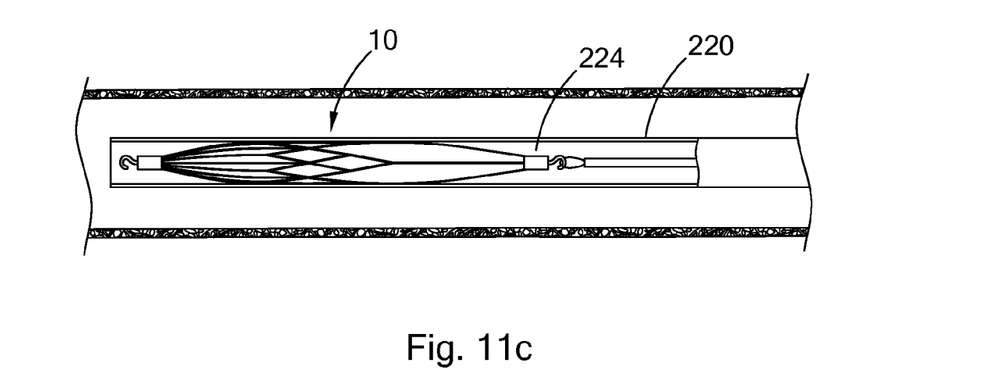

As indicated in box 504, and as illustrated in FIG. 11b, the method 500 further comprises advancing the retrieval sheath 220 distally in the direction of arrow A over the filter 10 while holding the control member 230 in a stationary position. As the retrieval sheath 220 is advanced distally, the distal end 222 of the retrieval sheath 220 contacts the secondary struts 40 of the filter 10. As the advancement of the retrieval sheath 220 continues, the distal end 222 of the retrieval sheath 220 rides over the secondary struts 40, collapsing the filter 10. Ultimately, as shown in FIG. 11c, the entire filter 10 is accommodated in the sheath lumen 224. As indicated in box 505, the retrieval assembly and the filter 10 are then removed from the patient's vasculature.

While the present invention has been described in terms of certain preferred embodiments, it will be understood that the invention is not limited to the disclosed embodiments, as those having skill in the art may make various modifications without departing from the scope of the following claims.

The invention claimed is:

1. An intravascular filter configured for bidirectional retrieval, comprising:
   a plurality of primary struts having first and second ends, the first ends being attached together along a longitudinal axis to define a downstream end of the filter, the primary struts extending upstream from the first ends to the second ends;
   a lattice portion substantially cylindrically disposed about the longitudinal axis, the lattice portion having upstream and downstream edges, the second ends of the primary struts adjoining the downstream edge;
   a plurality of secondary struts having third and fourth ends, the third ends adjoining the upstream edge of the lattice portion, the secondary struts extending upstream from the third ends to the fourth ends, the fourth ends being attached together along the longitudinal axis to define an upstream end of the filter;
   the lattice portion further comprising:
      a plurality of first connecting members, each of the plurality of the first connecting members extending from a second end of a primary strut to a second end of an adjacent primary strut;
      a plurality of second connecting members, each second connecting member adjoining the second end of one of the primary struts and extending to the third end of one of the secondary struts, two second connecting members adjoining the third end of each secondary strut; and
      a plurality of third connecting members, each third connecting member having a fifth end extending upstream from the second end of one of the primary struts and a sixth end adjoining one of the second connecting members;
   a first coupling element disposed at the downstream end of the filter for jugular vein retrieval; and
   a second coupling element disposed at the upstream end of the filter for femoral vein retrieval, the second coupling element housing only the fourth ends of the secondary struts.

2. The intravascular filter of claim 1, wherein each second connecting member has a primary end adjoining the second end of one of the primary struts and a secondary end adjoining the third end of one of the secondary struts, each third connecting member adjoining one of the secondary connecting members between the primary end and the secondary end.

3. The intravascular filter of claim 1, wherein two second connecting members adjoin the second end of every fourth primary strut, and no second connecting members adjoin any other primary strut.

4. The intravascular filter of claim 1, wherein the filter includes a first number of primary struts and a second number of secondary struts, the first number being greater than the second number.

5. The intravascular filter of claim 4, wherein the first number is four times as great as the second number.

6. The intravascular filter of claim 5, wherein the first number is sixteen, and the second number is four.

7. The intravascular filter of claim 1, wherein the secondary struts are longer than the primary struts.

8. The intravascular filter of claim 1, wherein each primary strut extends arcuately in a longitudinal plane, each primary strut including a first arc and a second arc, the first arc extending from the first end away from the longitudinal axis, the second arc extending from the first arc toward the longitudinal axis and terminating at the second end.

9. The intravascular filter of claim 8, further comprising an anchoring hook disposed on one of the primary struts.

10. The intravascular filter of claim 1, wherein the primary struts, the lattice portion, the secondary struts, the first coupling element, and the second coupling element are constructed from a laser cut nitinol cannula.

11. The intravascular filter of claim 10, wherein the first and second coupling elements each comprise a diagonal notch in the nitinol cannula.

12. The intravascular filter of claim 1, wherein the primary struts, the lattice portion, and the secondary struts are constructed from stainless steel wire.

13. The intravascular filter of claim 12, further comprising a downstream hub disposed at the downstream end of the filter and an upstream hub disposed at the upstream end of the filter, the downstream hub housing the first ends of the primary struts, the upstream hub housing the fourth ends of the secondary struts.

14. The intravascular filter of claim 13, wherein the first coupling element comprises a jugular retrieval hook extending downstream from the downstream hub, and the second coupling element comprises a femoral retrieval hook extending upstream from the upstream hub.

* * * * *

UNITED STATES PATENT AND TRADEMARK OFFICE
CERTIFICATE OF CORRECTION

| | | |
|---|---|---|
| PATENT NO. | : 9,011,479 B2 | Page 1 of 1 |
| APPLICATION NO. | : 13/328663 | |
| DATED | : April 21, 2015 | |
| INVENTOR(S) | : Cleve Koehler | |

It is certified that error appears in the above-identified patent and that said Letters Patent is hereby corrected as shown below:

On the Title Page

Insert --(73) Assignee:  COOK MEDICAL TECHNOLOGIES LLC
                           Bloomington, IN USA--

Signed and Sealed this
Fifth Day of January, 2016

Michelle K. Lee
*Director of the United States Patent and Trademark Office*